United States Patent [19]

Halasz et al.

[11] 4,196,145
[45] Apr. 1, 1980

[54] DYEING KERATIN FIBERS WITH 2-SUBSTITUTED M-TOLUENEDIAMINES

[75] Inventors: Alexander Halasz, Norwalk; David Cohen, Stamford, both of Conn.

[73] Assignee: Clairol Incorporated, New York, N.Y.

[21] Appl. No.: 867,724

[22] Filed: Jan. 9, 1978

Related U.S. Application Data

[62] Division of Ser. No. 716,052, Aug. 20, 1976, Pat. No. 4,092,102, which is a division of Ser. No. 406,442, Oct. 15, 1973, abandoned.

[51] Int. Cl.² .............. C07C 143/75; C07C 143/79; C07C 91/06; C07C 87/62
[52] U.S. Cl. .............. 260/573; 260/556 A; 260/577; 260/576; 260/556 AR; 260/465 E
[58] Field of Search .............. 260/556 A, 573, 577

[56] References Cited

U.S. PATENT DOCUMENTS

| | | | |
|---|---|---|---|
| 2,663,732 | 12/1953 | Neissberger | 260/556 A |
| 2,750,326 | 6/1956 | Eckardt et al. | 260/573 X |
| 2,943,109 | 6/1960 | Ramsay | 260/573 X |
| 2,992,192 | 7/1961 | Ingberman | 260/573 UX |
| 3,184,387 | 5/1965 | Seemuller | 260/573 UX |
| 3,591,638 | 7/1971 | Halasz | 260/577 X |
| 3,920,739 | 11/1975 | Suda et al. | 260/556 A |

FOREIGN PATENT DOCUMENTS

| | | | |
|---|---|---|---|
| 536577 | 5/1941 | United Kingdom | 260/556 A |
| 642422 | 9/1950 | United Kingdom | 260/573 |

Primary Examiner—Thomas A. Waltz
Attorney, Agent, or Firm—Irving Holtzman; George A. Mentis; David J. Mugford

[57] ABSTRACT

Oxidation dye compositions particularly useful for dyeing human hair containing as the meta component compounds of the formula:

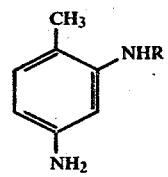

or their non-toxic salts, wherein R is alkyl, hydroxyalkyl, phenylalkyl, phenylsulfonyls, alkylsulfonyls or cyanoalkyl.

2 Claims, No Drawings

DYEING KERATIN FIBERS WITH 2-SUBSTITUTED M-TOLUENEDIAMINES

This is a division of application Ser. No. 716,052, filed Aug. 20, 1976, now U.S. Pat. No. 4,092,102, which is a division of Ser. No. 406,442, Oct. 15, 1973, now abandoned.

This invention relates to compositions and methods for dyeing keratin fibers using certain 2-substituted m-toluenediamines and to certain novel compounds of this class. More particularly, it concerns compositions and methods for dyeing human hair, either in the form of a wig or as natural hair on the human head, which employ 2-substituted m-toluenediamines of the formula:

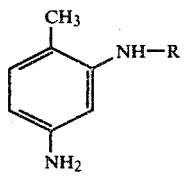

or their non-toxic salts (e.g. HCl, HBr, $H_2SO_4$, acetate, etc. salts), wherein R is alkyl, hydroxyalkyl, phenylalkyl, phenylsulfonyls, alkylsulfonyls (e.g. $CH_3SO_2$—) and cyanoalkyl (e.g. —$CH_2CN$).

It is known that in the present state of the hair dye art that only the so-called oxidation dyes give permanent dyeing in all shades. Practically all permanent dyes are formulated as oxidation dye compositions which give a large variety of shades, especially the natural ones. These dye compositions are formulated as mixtures of para components as, for example, aromatic diamines, aminophenols or phenols; and meta components as, for example, m-toluenediamine, m-phenylenediamine. The mixture of para and meta components reacts on the hair in the presence of hydrogen peroxide to form colors.

The shades obtained with these dye compositions are permanent and resistant to shampooings. However, the dyeings are not entirely satisfactory because the darker shades, especially the blue components of these shades, have a tendency to go redder with time. This reddening is accentuated by perspiration and sunlight. After a month, for example, the hair shows an unpleasant reddish cast.

It has now been found that when substituted m-toluenediamines of Formula I above are used as meta components in oxidation dye compositions, dye shades are obtained on hair that are fast to perspiration and light and which do not undergo a further oxidation toward reddish hues. The shades obtained are also more resistant to repeated shampooings (i.e. washfast) with considerably less change in color than with m-toluenediamine. They also give a better coverage, i.e. the dyeings exhibit the same intensity of color with less dye than, for example, 2,4-diaminoanisol, another meta component used in hair dyes.

It is accordingly an object of the present invention to provide dye compositions and particularly hair dye compositions of the permanent type which when dyed on hair are more resistant to off color wearing; are more wash fast, light fast and perspiration fast than prior art compositions of this character.

It is also an object of the present invention to provide hair dye compositions of the aforesaid type and having the aforesaid properties which employ as the meta component in oxidation dye compositions a compound of Formula I above.

It is a further object of this invention to provide methods for dyeing keratin fibers and particularly human hair which employs the aforesaid hair dye compositions.

Other and more detailed objects of this invention will be apparent from the following description and claims.

In the 2-substituted m-toluenediamine described above in Formula I the chain length of the alkyl chain or alkyl moiety of the compound radicals (e.g. hydroxyalkyl, phenylalkyl) may vary. Ordinarily, the alkyl chain or alkyl moiety will be of the lower chain length variety containing 1 to 6 carbon atoms. When R is a hydroxyalkyl radical it will ordinarily contain from 1 to 3 hydroxy groups.

To further illustrate more specifically the various values that R may have in Formula I the following are given:

(1) R=alkyl; methyl, ethyl, n-propyl, isopropyl, n-butyl, isobutyl, ter-butyl, pentyl, hexyl.

(2) R=hydroxyalkyl: (preferably 2 to 6 carbon atoms and 1 to 3 hydroxy groups); hydroxymethyl, 2-hydroxyethyl, 3-hydroxypropyl; 2,3-dihydroxypropyl, 4-hydroxybutyl; 1,3-dihydroxypropyl, 4-hydroxybutyl; 1,3-dihydroxypropyl, tris(hydroxymethyl)methyl.

(3) R=phenylalkyl; benzyl, phenylethyl, phenylpropyl, methylbenzyl

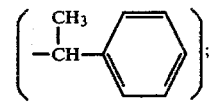

methylphenylethyl

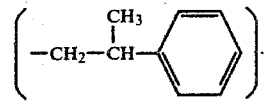

(4) R=alkylsulfonyl or phenylsulfonyls: methylsulfonyl ($CH_3$—$SO_2$—); ethylsulfonyl ($C_2H_5$—$SO_2$—); propylsulfonyl ($CH_3$—CH—$CH_2SO_2$—), phenylsulfonyl

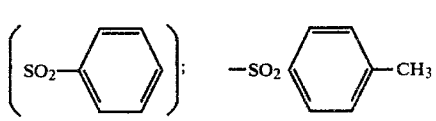

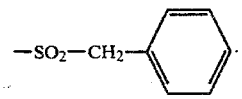

(5) R=cyanoalkyls: cyanomethyl (—$CH_2$—CN); cyanoethyl (—$CH_2$—$CH_2$—CH); cyanopropyl (—$CH_2$—$CH_2$—$CH_2CN$); cyanobutyl (—$CH_2(CH_2)_3CN$).

Among the above groups of compounds it has been found that the best results are obtained with those compounds in which R is alkyl or hydroxyalkyl. These, accordingly, form a preferred group of meta components which can be advantageously used in oxidation dye compositions in accordance with the present invention.

The 2-substituted m-toluenediamines employed in the present invention may be readily prepared using reactions that are well known in the prior art. The reaction of choice will depend upon the particular substituent that is introduced into the amine nitrogen. Below are given some of the typical reactions for preparing these compounds:

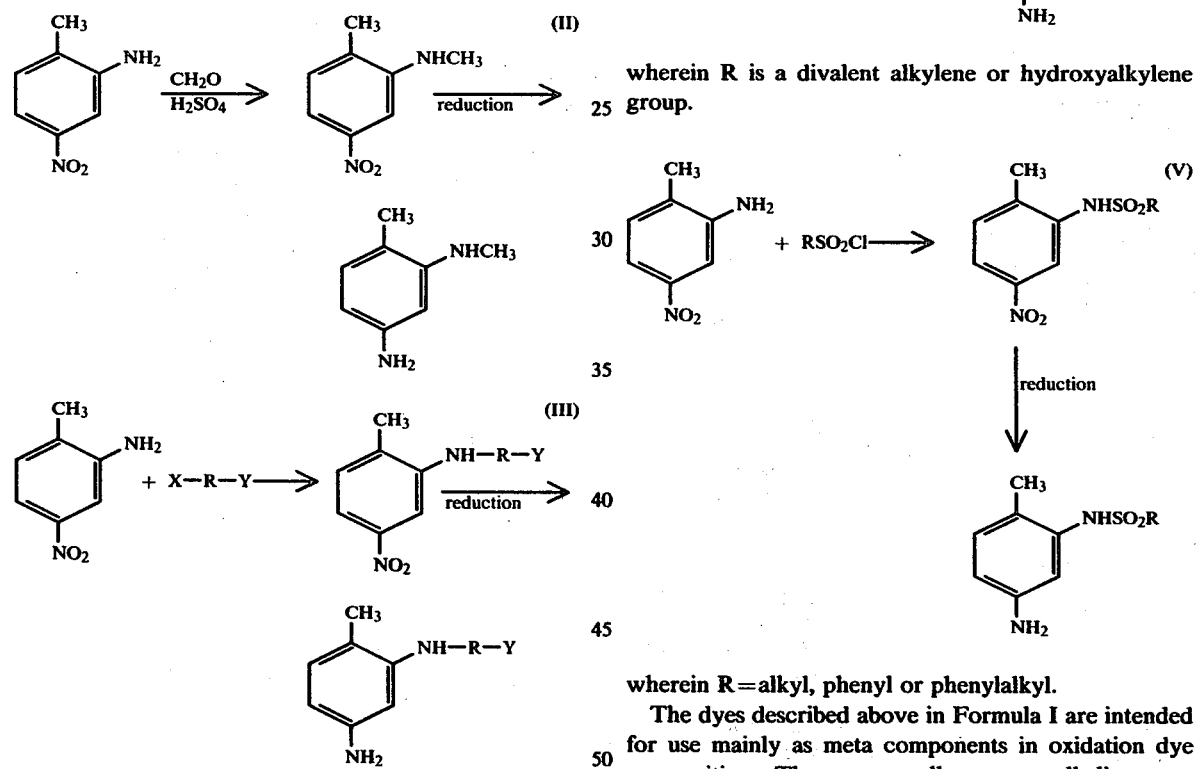

Wherein:

X = halogen

Y = H, OH, CN

R = the divalent radicals; alkylene (e.g. —CH$_2$—CH$_2$—), phenylalkylene

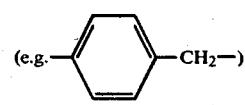

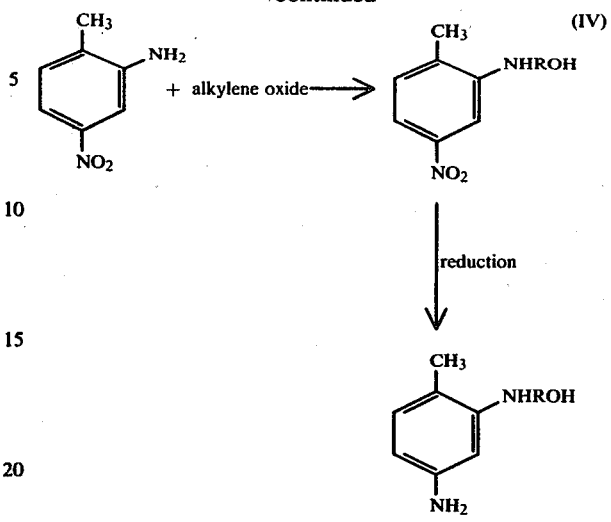

wherein R is a divalent alkylene or hydroxyalkylene group.

wherein R = alkyl, phenyl or phenylalkyl.

The dyes described above in Formula I are intended for use mainly as meta components in oxidation dye compositions. These are usually aqueous alkaline compositions that contain, in addition to the meta component, at least one para component. Optionally, such composition may also contain such things as modifier dye intermediates, nitro dyes, soaps, surfactants, thickening agents, antioxidants and organic solvents. Furthermore, these aqueous compositions may take various forms such as solutions, flowable liquids, pastes, creams or gels.

Illustrations of the para components that may be used in this invention mention may be made of the following: p-toluenediamine, p-aminophenol, p-aminodiphenylamine, 4-4'-diaminodiphenylamine, p-phenylenediamine, 2,6-dimethyl-p-phenylenediamine, 2,5-diaminopyridine. Of special interest is a class of para components described by the formula:

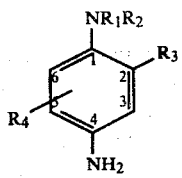

or its non-toxic salts, in which:

R₁ is alkyl or hydroalkyl;

R₂ is hydrogen or hydroxyalkyl;

R₃ is hydrogen, alkyl, alkoxy or halogen; and

R₄ occupies any one of the remaining positions on the benzene radical and is hydrogen, alkyl, alkoxy or halogen; providing that R₂ is hydrogen when R₃ is alkyl, alkoxy or halogen and providing that at least two of R₁, R₂, R₃ or R₄ are other than hydrogen. In this case too the alkyl groups or alkyl moieties contain 1 to 6 carbon atoms and the hydroxyalkyl contains from 1 to 3 hydroxy groups. The halogen may be Cl, Br, Fl, I, etc.

In addition to the meta and para components, the oxidation dye compositions of this invention may contain other modifier dye intermediates. These include such things as the m-aminophenols, compounds containing active methylene groups, phenols, etc. m-Aminophenols can give either indophenols or indamines on oxidative coupling with para components. The products are usually violet in color and are used in modifying shades. Examples of aminophenols useful herein are 2,4-diaminophenol, m-aminophenol, aminoresorcinol, 1,5-aminohydroxynaphthalene and 1,8-aminohydroxynaphthalene.

Compounds containing active methylene groups are also capable of reacting with the oxidatively activated para components. The products are imino compounds of various types and are yellow or red in color. Examples of active methylene compounds employable in the present invention are 3-methylpyrazolone-(5), 1-phenyl-3-methylpyrazolone-(5); 1,3-dimethylpyrazolone-(5), acetoacetic acid anilide, benzoylacetotoluide and nicotinoylacetanilide.

Still other oxidation dye intermediates, i.e. modifiers, may be present in the compositions of this invention which produce colored products under oxidative conditions by more complex mechanisms. This may include one or more of self-coupling, or coupling with the para components or with other intermediates present. Among these may be mentioned hydroquinone, catechol, 1,5-naphthalenediol, o-phenylenediamine, o-aminophenol.

Phenols react with para components, in the presence of oxidizing agents, to produce indophenols. These are usually blue or violet compounds, although resorcinols give yellow or brown colored compounds under these conditions. The brown colors obtained from the reaction of resorcinols are commonly used to produce the depth of a shade. Examples of phenols useful in oxidation dye compositions of this invention are pyrogallol, resorcinol, pyrocatechol and alphanaphthol.

It is sometimes desirable to add to said oxidation dye mixture dyes which are already colored i.e. which do not require an oxidizing agent for color development. These are generally added for blending purposes to obtain natural looking colors in the final dyeing operation. One class of dyes which may be used for this purpose is the nitro dyes and this component is generally referred to herein as the nitro dye component. A large number of nitro dyes are known in the prior art which are suitable for this purpose. The only limitation that is placed on a nitro dye to be useful in the present invention is that it be one whose color is not destroyed by the oxidizing agent used in the final color development of the oxidizable components. By way of illustrating suitable nitro dyes, mention may be made of the following: 4-nitro-o-phenylenediamine, 2-nitro-p-phenylenediamine, 4-nitro-2-aminophenol, 5-nitro-2-aminophenol, 2-nitro-4-aminophenol and picramic acid.

The pH of the oxidation dye mixture of this invention will generally be on the basic side e.g. 8-11. It is preferred, however, that this pH be in the range of about 9-10.

Any of a wide variety of alkalizing agents can be used to adjust the pH of the dyeing composition on the basic side. Ammonium hydroxide, because of its freedom from toxicity over a wide concentration range and its economy, is an acceptable alkalizing agent. However, there can be used in place of, or together with, ammonia any other compatible ammonia derivative as an alkalizing agent, such as an alkylamine, such as ethylamine, or triethylamine; or alkanolamine, such as monoethanolamine or diethanolamine. Likewise, any other of the common alkalizing agents may be used, such as sodium or potassium hydroxide, sodium or potassium carbonate, sodium phosphate, sodium hydrogen phosphate, sodium silicate, and the like.

Among the soaps which may be present in the compositions of this invention may be mentioned the sodium, ammonium or potassium salts of lauric, stearic, palmitic, oleic, linoleic or ricinoleic acid. The soaps may be present to the extent of 5-35% of the weight of the oxidation dye mixture, and preferably 15-25%.

Among the surface active agents useful in the present invention, mention may be made of the water-soluble surface active agents. These can be anionic, non-ionic or cationic. Illustrative of the various types of water-soluble surface active agents there can be mentioned: higher alkylbenzenesulfonates; alkylnaphthalenesulfonates; sulfonated esters of alcohols and polybasic acids; taurates; fatty alcohol sulfates; sulfates of branched chain or secondary alcohols; alkyl dimethylbenzyl ammonium chlorides; and the like. Illustrative of specific surfactants there can be mentioned: sodium lauryl sulfate; polyoxyethylene lauryl ester; myristyl sulfate; glyeryl monostearate; sodium salt of palmitic methyl taurine; cetyl pyridinium chloride; lauric diethanolamide; polyoxyethylene stearate; stearyl dimethyl benzyl ammonium chloride; dodecyl benzene sodium sulfonate; nonyl naphthalene sodium sulfonate; dioctyl sodium sulfosuccinate; sodium N-methyl-N-oleoyl taurate; oleic acid ester of sodium isothionate; sodium dodecyl sulfate; the sodium salt of 3,9-diethyl-tridecanol-6-sulfate and the like. The quantity of water-soluble surface active agent when present can vary over a wide range, such as that of from about 0.5% to 30% by weight of the composition, and preferably 1-10%.

Various organic solvents may also be present in the oxidation dye mixture for the purpose of solubilizing a dye intermediate or any other component which may be insufficiently soluble in water. Generally, the solvent selected is such as to be miscible with water and innocous to the skin, and includes for example, ethanol, isopropanol, glycerine, ethylene glycol, propylene glycol, ethylene glycol monoethyl ether, diethylene glycol, diethylene glycol monoethyl ether, etc. The amount of solvent used may vary from 1–40% of the oxidation dye mixture, and preferably 5–30%.

To exemplify the thickening agents that can also be incorporated in the present dyeing composition, mention may be made of sodium alginate or gum arabic, or cellulose derivatives, such as methylcellulose, hydroxyethylcellulose, or the sodium salt of carboxymethylcellulose, or acrylic polymers, such as polyacrylic acid sodium salt, or inorganic thickeners, such as bentonite. The quantity of thickening agent when present can vary over a wide range, such as that of from about 0.5% to 5% and preferably from about 0.5% to 3% by weight.

To illustrate the antioxidants that may be used in the present oxidation dye mixture, mention may be made of sodium sulfite, thioglycollic acid, sodium hydrosulfite and ascorbic acid. The quantity of antioxidant that may be contained in the instant oxidation dye mixture will usually be in the range of from about 0.05% to 1% by weight based on the total weight of the oxidation dye mixture.

Water is ordinarily the major constituent of the present composition and can vary over a wide range dependent in large measure on the quantity of other additives. Thus, the water content can be as little as 20% and preferably from about 30% to 90%.

The dyeing compositions of this invention are preferably aqueous compositions. The term "aqueous composition" is used herein in its usual generic sense as embracing any water-containing composition embodied in the invention. This includes true solutions or mixtures of the dye in an aqueous medium, either alone or in conjunction with other materials, which are also dissolved or dispersed in the aqueous medium. The dye may be colloidally dispersed in the medium or may merely be intimately mixed therein.

To further illustrate the various other modifiers, antioxidants, alkalizers and other adjuvants that may be incorporated in the oxidation dye mixture of this invention, reference is made to Sagarin "Cosmetics, Science and Technology" (1957), pages 505–507, Interscience Publishers, Inc., New York. The aqueous compositions of this invention may take many forms. Thus, they may be thin or thick flowable liquids, pastes, creams, gels, etc.

To summarize the various components that may comprise the oxidation dye mixture of this invention, Table I below is given. The percentages are given as percent by weight based on the total weight of the oxidation dye mixture.

TABLE I

| Components | % by weight | |
| --- | --- | --- |
| | General | Preferred |
| Para component | 0.1 to 6 | 0.2 to 4 |
| New meta component | 0.1 to 6 | 0.2 to 4 |
| Other oxidation dye intermediate | 0 to 4 | 0.1 to 2 |
| Nitro dyes | 0 to 3 | 0.01 to 2 |
| Soap | 0 to 35 | 15 to 25 |
| Surfactant | 0 to 30 | 1 to 10 |
| Thickening agent | 0 to 5.0 | 0.05 to 3 |
| Antioxidants | 0 to 1.0 | 0.05 to 1 |
| Organic solvents | 0 to 40 | 5 to 30 |
| Water | QS to 100% | |
| Alkalizing agent to pH | 8 to 11 | 9 to 10 |

The aforesaid oxidation dye mixtures of this invention are intended for use in conjunction with conventional oxidation dye "developers", which contain the oxidizing agent necessary to effect reaction to colored products. Typical developers that are useful for this purpose are aqueous solutions of hydrogen peroxide, e.g. 5 to 12%, or high viscosity creams containing in addition, for example, nonylphenol polyethylene glycol or lauryl alcohol polyethylene glycol, in an amount of from 2–10% of the weight of developer, or crystalline peroxide such as urea peroxide or melamine peroxide.

In use, a quantity of the developer described above is mixed with a quantity of oxidation dye composition described previously. Usually, the amount of developer taken is far in excess of that required to oxidize the intermediates, the amounts taken being dependent on the form and concentration of the developer selected. The mixture is well shaken and applied to hair. It can be applied as a shampoo to the entire head, applied to one area of the hair, such as the roots and combed through the rest of the hair later. The mixture is allowed to remain on the head for a period of time and is then removed by shampooing. The normal time of application is 20–30 minutes, but application times of from 10 minutes to one hour can be used.

In one form of application of the compositions of this invention, the oxidation dye mixture is dispensed from an aerosol container under pressure of a suitable propellant. The foam so obtained is mixed with the developer, generally a solution of hydrogen peroxide, and applied to the hair as above.

The following Examples are given to further illustrate the present invention. It is to be understood, however, that the invention is not limited thereto. Unless otherwise specified, all percentages are given as percent by weight based on the total weight of the composition.

The following expressions used in the Examples have the meanings indicated below:

Carbopol 934—This is a water-soluble polymer of acrylic acid cross linked with about 1% of a polyallyl ether of sucrose having an average value of about 5.8 allyl groups for each molecule of ether and having a molecular weight in the order of magnitude of 1,000,000.

Dupanol C—Sodium lauryl sulfate, U.S.P. grade.

EXAMPLE 1

Preparation of 2-methylamino-4-aminotoluene 15.4 g. (0.1 M) of 2-amino-4-nitrotoluene was dissolved in 100 ml. 96% $H_2SO_4$ at room temperature with stirring and 50 ml. of a 36% solution of formaldehyde in $H_2O$ was added. The mixture was stirred for 30 minutes and poured on ice, neutralized with NaOH, filtered and washed. There was obtained 16.1 g. of 2-methylamino-4-nitrotoluene; m.p. 107°–108° (Gnehm/Blume. Ann. 304, 100, gives 107.5° C.). 8.3 g. of the above compound was reduced catalytically with Pd as catalyst and the free amine produced was reacted with HCl to form 10 g. of the dihydrochloride (the free amine is liquid).

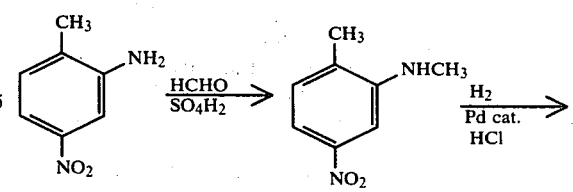

-continued

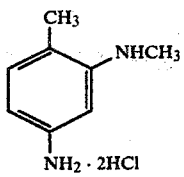

EXAMPLE 1A

Dye Test of 2-methylamino-4-aminotoluene with p-phenylenediamine 0.104 g. (0.0005 M) 2-methylamino-4-aminotoluene dihydrochloride (meta component) and 0.054 g. (0.0005 M) p-phenylenediamine (para component) was added to 3 ml. of ethanol and 20 g. of an aqueous solution composed of 1% Carbopol 934 (thickening agent) 0.1% Dupanol C (surfactant) and 3.8% ammonium acetate. The mixture was stirred with 3 ml. ammonium hydroxide (28%) and 20 ml. 6% hydrogen peroxide. A sample of human hair was dyed with this composition for 30 minutes at 30° C. A blue color was obtained which was perspiration, light and washfast, and superior in these characteristics to a similar dyeing obtained in which m-toluenediamine was used as the meta component.

EXAMPLE 1B

Dye Test of 2-methylamino-4-aminotoluene using p-toluenediamine sulfate as para component 0.109 g. (0.0005 M) 2-methylamino-4-aminotoluene hydrochloride and 0.11 g. (0.005 M) p-toluenediamine sulfate were dissolved in 3 ml. ethanol and in a 20 cc. base made up of 1% Carbopol 934, 0.1% Dupanol, C, 3.8% ammonium acetate and water. To this solution was added 3 ml. 28% ammonium hydroxide and 20 ml. 6% hydrogen peroxide. The resulting mixture was dyed on a sample of human hair for 30 minutes at 30° C. The hair was dyed blue which was perspiration, light and washfast.

EXAMPLE 2

Preparation of 2-ethylamino-4-aminotoluene

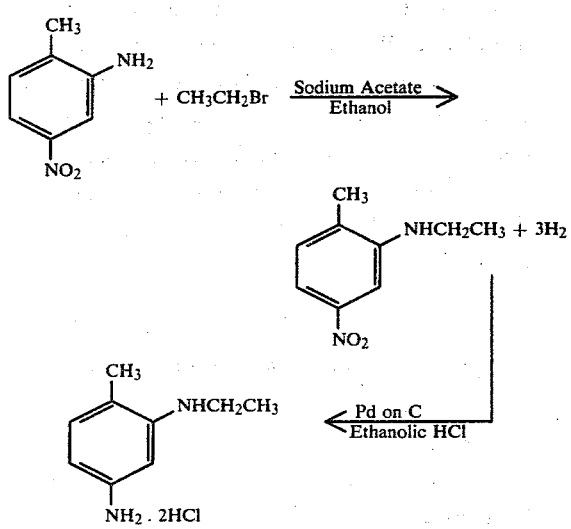

Starting Material:
A. 15.2 g. (0.1 M) 2-methyl-5-nitroaniline
B. 21.8 g. (0.2 M) Ethyl bromide
C. 13.6 g. (0.1 M) Sodium acetate 0.3H$_2$O
D. 100 ml. Ethanol Procedure:

A, B, C and D were placed in a small autoclave and heated on a oil bath to 120°–125° C. for 22 hours. The reaction mixture was cooled and filtered and the filtrate was evaporated on a rotovac. The resulting solid was recrystallized from EtOH-H$_2$O mixture to yield 7.9 g. yellow-brown crystals (Mac Callum, Soc. 67, 247). 4.5 g. of the above product was catalytically reduced with Pd and subsequently converted to the dihydrochloride. Weight of product=4.36 g. The 2-ethylamino-4-aminotoluene prepared by this Example was dyed out using the process of Examples 1A and 1B above in which the 2-ethylamino-4-aminotoluene was used in place of the 2-methylamino-4-aminotoluene as the meta component. These dyeings produced deep blue shades with good perspiration fastness.

EXAMPLE 3

Preparation of 2-propylamino-4-aminotoluene

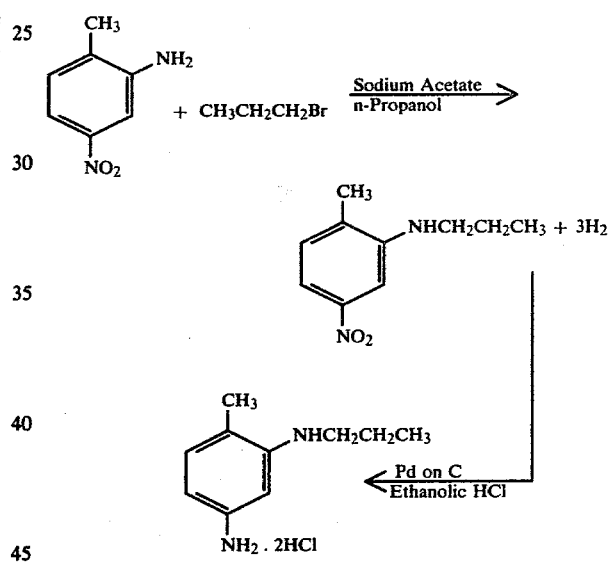

Starting Material:
A. 15.2 g. (0.1 M) 2-methyl-5-nitroaniline
B. 61.5 g. (0.5 M) 1-bromopropane
C. 13.6 g. (0.1 M) Sodium acetate 0.3H$_2$O
D. 125 ml. n-propanol Procedure:

A, B, C, and D were placed in a 500 ml. 3 neck flask and heated by a heating mantle, with stirring, to reflux. The reaction was complete after 54 hours of reflux as determined by a thin layer chromatogram. The reaction mixture was cooled and filtered to eliminate salt. The solvent was evaporated from the filtrate on a rotary evaporator. The resulting solid material was recrystallized from H$_2$O. Orange oil insoluble in hot water was separated by decantation. The oil which solidifies on cooling is the product. Weight of product=7.0 g. M.P.=54°–59° C. The product had a faint trace of impurity. 4.85 g. of the above product was catalytically reduced with Pd and subsequently converted to the dihydrochloride. Weight of product recovered=5.44 g. Subsequent dye tests with various para components, e.g. PPD and PTD, produced deep blue shades with good perspiration fastness. The 2-propylamino-4-aminotoluene prepared by this Example was dyed out using the process of Examples 1A and 1B in which the 2-propylamino-4-aminotoluene was used in place of the 2-methylamino-4-aminotoluene as the meta component. These dyeings produced deep blue shades with good perspiration fastness.

EXAMPLE 4

Preparation of 2-hydroxyethylamino-4-aminotoluene

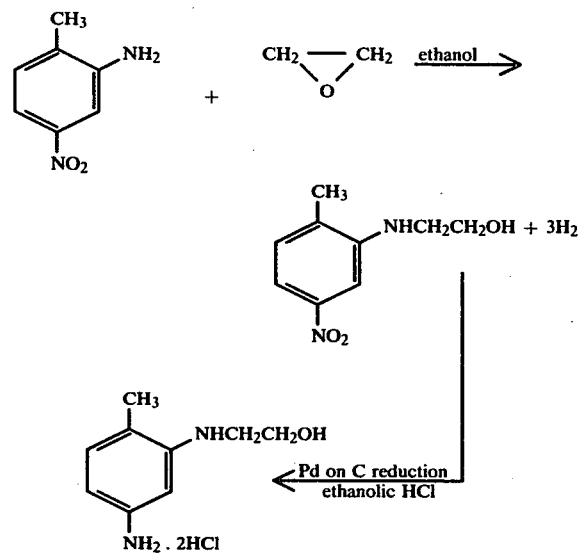

Starting Material:
A. 30.4 g. (0.2 M) 2-amino-4-nitrotoluene
B. 130 g. Ethanol 3A
C. Ethylene oxide (enough to complete reaction)

Procedure:

A and B were mixed in a 500 ml. 3 neck flask equipped with a stirrer and reflux condenser. The reaction mixture was heated to reflux by means of a heating mantle, and C was then slowly bubbled into the reaction mixture through a trap containing 10 ml. xylene. The ethylene oxide was bubbled through until reaction is completed as indicated on thin layer chromatogram (total time approximately 50 hours). The resulting solution was evaporated of solvent on a rotary evaporator. The solid that remains was recrystallized from deionized water. Weight of orange-red product obtained was 11.2 g. (m.p.=89°-90° C.) % N found=14.26 Theory=14.28 9 g. of the above product was catalytically reduced on a Parr hydrogenator using 5% Palladium on carbon as catalyst in an ethanol solvent. The resulting reduced material filtered into ethanolic HCl (prepared by bubbling HCl gas into ethanol). After all the solvent is evaporated, a white solid product results. The 2-hydroxyethylamino-4-aminotoluene prepared by this Example was dyed out using the process of Examples 1A and 1B in which the 2-hydroxyethylamino-4-aminotoluene was used in place of the 2-methylamino-4-aminotoluene as the meta component. These dyeings produced deep blue shades with excellent perspiration fastness.

EXAMPLE 5

Preparation of 2-benzylamino-4-aminotoluene

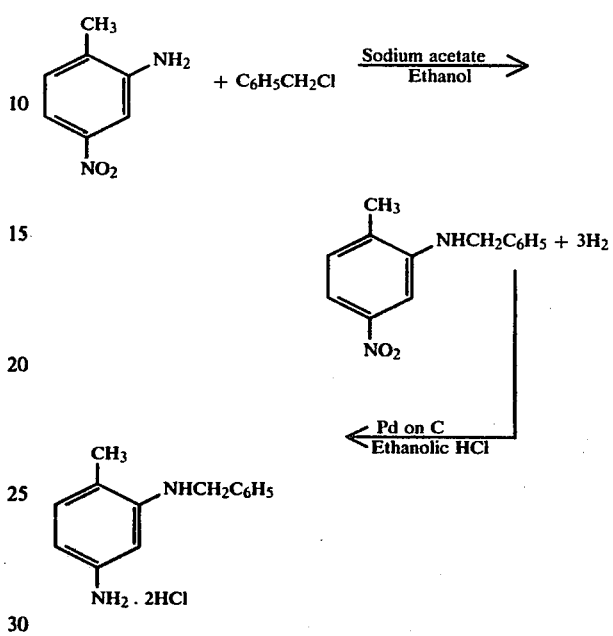

Starting Material:
A. 15.2 g. (0.1 M) 2-methyl-5-nitroaniline
B. 28.0 g. (0.2 M+10% excess) benzyl chloride
C. 13.6 g. (0.1 M) Sodium acetate 0.3H$_2$O
D. 100 ml. ethanol Procedure:

A, B, C and D were heated in an autoclave at 125° for 22 hours, cooled and filtered. No recrystallization was necessary. Weight of product=11.4 g. m.p.=124°-125° C. (Ullmann, Grether, Berichte 35, 338, gives 124° C.). 6.05 g. of above product was reduced and converted to dihydrochloride. Weight of product=6.78 g. The 2-benzylamino-4-aminotoluene prepared by this Example was dyed out using the process of Examples 1A and 1B above in which the 2-benzylamino-4-aminotoluene was used in place of the 2-methylamino-4-aminotoluene as the meta component. These dyeings produced blue shades.

EXAMPLE 6

Preparation of 2-methylsulfamido-4-aminotoluene

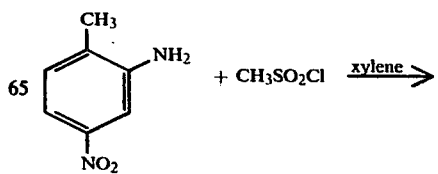

-continued

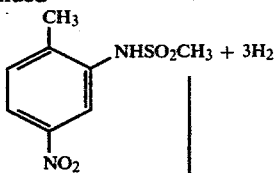

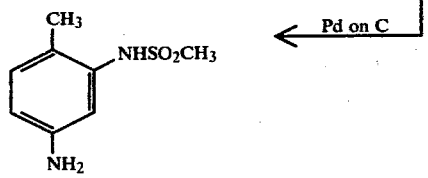

Starting Material:
A. 30.4 g. (0.2 M) 2-amino-4-nitrotoluene
B. 25.2 g. (0.22 M) methanesulfonyl chloride
C. 300 ml. xylene Procedure:

A and C were stirred and heated to reflux in a 1 l 3 neck flask. B was added dropwise. The reaction refluxed for 20 hours and the reaction was cooled and filtered. Solid material recovered was recrystallized from ethanol. The weight of product obtained = 30.0 g. m.p. = 146°-147° C. 23.0 g. (0.1 M) of the above intermediate was reduced with Pd on catalyst. The product was recrystallized from ethanol. The weight of product obtained = 7.3 g. m.p. = 173°-173.5° C. The 2-methylsulfamido-4-aminotoluene prepared by this Example was dyed out using the process of Examples 1A and 1B above in which the 2-methylsulfamido-4-aminotoluene was used in place of the 2-methylamino-4-aminotoluene as the meta component. These dyeings produced violet blue and deep blue shades respectively with p-phenylenediamine and p-toluenediamine as para component.

EXAMPLE 7

Preparation of 2-cyanomethylamino-4-aminotoluene

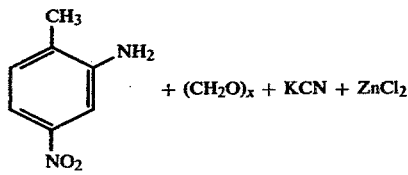

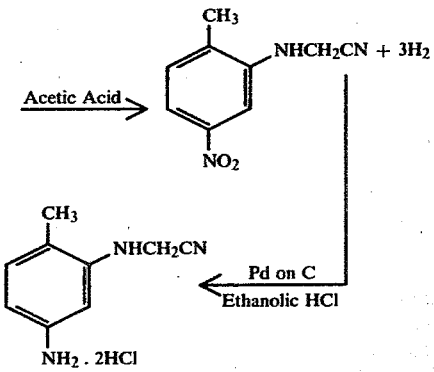

Starting Material:

A. 45.6 g. (0.3 M) 2-Methyl-5-nitroaniline
B. 27.0 g. Paraformaldehyde
C. 58.5 g. Potassium cyanide
D. 157.5 g. Zinc chloride
E. 1500 cc. acetic acid Procedure:

A, B, C and D were placed in a 3 l. 3 neck flask and cooled by an ice bath. E with 2 ml. conc. $H_2SO_4$ was added dropwise with stirring. After the addition the mixture was stirred for 30 minutes and the temperature was then raised to 50° C. over a one hour period. The reaction was stirred at 50° C. for an additional 8 hours. Contents of the flask were then cooled and poured into 2100 ml. ice water. The resulting solid was filtered and washed with water. The product was recrystallized from $H_2O$-EtOH mixture. M.P. of yellow crystals = 148°-149° C. Analysis:

|  | Theory | Found |
|---|---|---|
| %C | 56.54 | 56.12 |
| H | 4.71 | 4.86 |
| N | 21.98 | 21.40 |

Weight of product = 28.7 g. 6.4 g. of above product was catalytically reduced with Pd and subsequently converted to dihydrochloride. Weight of product = 8.67 g. The cyanomethylamino-4-aminotoluene prepared by this Example was dyed out using the process of Examples 1A and 1B above in which the 2-cyanomethylamino-4-aminotoluene was used in place of the 2-methylamino-4-aminotoluene as the meta component. These dyeings produced gray-blue shades.

EXAMPLE 8

One ounce of a solution of the following composition is prepared:

| N,N-bis(2-hydroxyethyl)-p-phenylenediamine hydrochloride | 1% |
|---|---|
| 2-Methylamino-4-aminotoluene | 1% |
| oleic acid | 35% |
| ammonium hydroxide (28% Aq.) | 8% |
| isopropanol | 20% |
| water | 41% |

This solution is mixed with 1 oz. of 6% aqueous hydrogen peroxide and applied to a swatch of gray hair for 20 minutes at ambient temperature. The hair is found to be dyed blue.

EXAMPLE 9

One ounce of a solution of the following composition:

| 2,6-dimethyl-p-phenylenediamine | .5% |
|---|---|
| N,N-bis(2,3-dihydroxypropyl)-p-phenylenediamine | .1% |
| resorcinol | .6% |
| 2-propylamino-4-aminotoluene | .1% |
| 4-nitro-o-phenylenediamine | .1% |
| 2-nitro-p-phenylenediamine | .1% |
| hydroxyethylcellulose | 1% |
| ammonium acetate | 4% |
| 28% aqueous ammonia | 10% |
| ammonium lauryl sulfate | .1% |
| water | 92% | is mixed with 1 oz. of 6% aqueous hydrogen peroxide and applied to gray hair for 20 minutes. The hair is found to be dyed brown.

EXAMPLE 10

One ounce of a solution of the following composition:

| | |
|---|---|
| N,2-dimethyl-p-phenylenediamine | 3.2% |
| resorcinol | 2.1% |
| 2-β-hydroxyethylamino-4-aminotoluene | .2% |
| o-phenylenediamine | .4% |
| 2-nitro-p-phenylenediamine | .2% |
| Carbopol 934 | 1.5% |
| ammonium acetate | 5% |
| ammonia (28% aqueous) | 12% |
| isopropanol | .5% |
| sodium lauryl sulfate | .2% |
| sodium sulfite | 0.7% |
| water | 83.5% | is mixed with 1 oz. of 6% aqueous $H_2O_2$ containing 1% Carbopol 934 and applied to gray hair for 20 minutes. The hair is found to be dyed chestnut.

EXAMPLE 11

One ounce of a solution of the following composition:

| | |
|---|---|
| 4-amino-2-methyl-N-(2-hydroxyethyl)-aniline hydrochloride | 3.5% |
| resorcinol | 3.5% |
| 2-ethylamino-4-aminotoluene | .2% |
| nitro-p-phenylenediamine | .1% |
| 4-nitro-o-phenylenediamine | .1% |
| oleic acid | 12% |
| ammonia | 1.5% |
| isopropanol | 7.5% |
| sodium lauryl sulfate | .1% |
| water | 71.5% | is mixed with 1 oz. of a solution of 1% Carbopol 934 in 6% aqueous hydrogen peroxide. The mixture is applied to gray hair for 30 minutes and produces dark brown.

EXAMPLE 12

One ounce of a solution of the following composition:

| | |
|---|---|
| N,3-dimethyl-p-phenylenediamine hydrochloride | 1.2% |
| resorcinol | 1.3% |
| 2-benzylamio-4-aminotoluene | .1% |
| nitro-p-phenylenediamine | .05% |
| oleic acid | 5% |
| diethanoamine | 2% |
| isopropanol | 5% |
| glycerine | .2% |
| water to 100% | | was mixed with 1 oz. of 6% aqueous hydrogen peroxide containing 1% hydroxyethylcellulose. The mixture was applied to gray hair for 30 minutes and then removed by shampooing. The hair was found to be dyed brown.

EXAMPLE 13

One ounce of a solution of the following composition:

| | |
|---|---|
| N-methyl-2-methoxy-p-phenylene- | |
| diamine | 3.5% |
| resorcinol | 3.3% |
| 2-methylsulfamido-4-aminotoluene | .1% |
| o-phenylenediamine | .5% |
| 4-nitro-o-phenylenediamine | .05% |
| 28% aqueous ammonia | 10% |
| ammonium acetate | 2.5% |
| water | 89.5% | was mixed with 0.5 oz. of 6% aqueous $H_2O_2$ and applied to a swatch of gray hair for 20 minutes. The dye was removed by rinsing and the hair on drying was found to be dyed brown.

EXAMPLE 14

One ounce of a solution of the following composition:

| | |
|---|---|
| p-phenylenediamine | 2.5% |
| resorcinol | 2.5% |
| N,N-bis(βhydroxyethyl)-3-methyl-p-phenylenediamine sulfate | 0.5% |
| 2-cyanoethylamin0-4-aminoootoluene | .2% |
| o-phenylenediamine | .7% |
| Carbopol 934 | 2% |
| 28% aqueous ammonia | 12% |
| sodium sulfite | 1.1% |
| sodium lauryl sulfate | .2% |
| water | 88.5% | is mixed with 1½ oz. of 4% aqueous hydrogen peroxide and applied to gray hair for 30 minutes. The hair is found to be dyed dark brown.

EXAMPLE 15

An oxidation dye composition is prepared of the following ingredients, in the weight percentages given:

| | |
|---|---|
| p-phenylenediamine | 2.6% |
| N,N-bis-(2-hydroxyethyl)-p-phenylenediamine sulfate | 0.4% |
| resorcinol | 1.0% |
| 2-methylamino-4-aminotoluene | 0.7% |
| 4-nitro-o-phenylenediamine | 0.06% |
| o-aminophenol | 0.15% |
| m-aminophenol | 0.3% |
| ethylenediamine tetraacetic acid | 0.04% |
| isopropanol | 10% |
| ammonium hydroxide 28% | 9% |
| sodium lauryl sulfate | 2.5% |
| sulfonated castor oil | 2.8% |
| carbitol (diethyleneglycol ethyl ether) | 4% |
| olec acid | 15% |
| propylene glycol | 4% |
| water to make 100% | |

Three ounces of the above composition is loaded into a co-dispensing aerosol can which employs the "OEL co-dispensing valve", as described in Sanders, "Principles of Aerosol Technology", pages 348–349.

The inner compartment (peroxide bag), a flexible polyethylene bag, is filled with the developer solution; namely, one ounce of 12% aqueous hydrogen peroxide, and the can is sealed with the introduction of 4.5 g of a propellant consisting of 35% 1,2-dichloro-1,1,2,2-tetrafluoroethane and 65% 1,1-difluoroethane. For application to hair the contents of the can are released as a foam consisting of an intimate mixture of the oxidation dye mixture and the developer in the ratio of 3:1. The foam is worked into the hair and is left on for twenty minutes, after which the hair is thoroughly rinsed. It is dyed dark brown.

Unless otherwise specified, all of the dyeings carried out in the above Examples are carried out at room temperature.

What is claimed is:

1. The compound of formula:

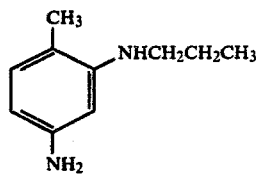

or its hydrochloride salts.

2. The compound of formula:

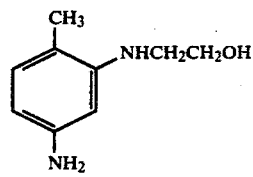

or its hydrochloride salts.

* * * * *